United States Patent [19]
Kutter et al.

[11] 3,985,891
[45] Oct. 12, 1976

[54] 2-PHENYL-IMIDAZO (4,5-b)PYRIDINES AND SALTS THEREOF

[75] Inventors: Eberhard Kutter; Volkhard Austel, both of Biberach an der Riss; Willi Diederen, Rissegg, all of Germany

[73] Assignee: Boehringer Ingelheim GmbH, Ingelheim am Rhein, Germany

[22] Filed: Aug. 22, 1975

[21] Appl. No.: 606,886

Related U.S. Application Data

[63] Continuation-in-part of Ser. No. 439,362, Feb. 4, 1974, abandoned.

[30] Foreign Application Priority Data

Feb. 3, 1973 Germany............................ 2305339
Dec. 12, 1973 Germany............................ 2361757

[52] U.S. Cl. ......................... 424/263; 260/294.8 C; 260/296 H
[51] Int. Cl.[2] .............. A61K 31/395; C07D 213/74
[58] Field of Search ..... 260/296 B, 296 H, 294.8 C; 424/263

[56] References Cited
OTHER PUBLICATIONS

Garmaise et al., Journal of Org. Chem. vol. 29, (11), pp. 3403–3405 Nov. 1964.

Primary Examiner—Alan L. Rotman
Attorney, Agent, or Firm—Hammond & Littell

[57] ABSTRACT

Compounds of the isomeric formulas

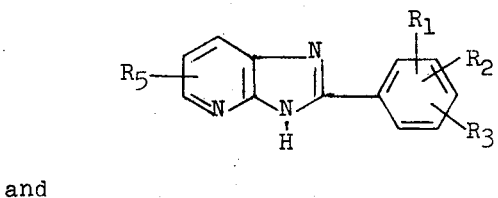

and

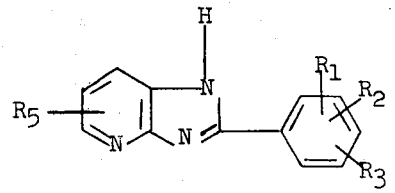

wherein
$R_1$ is alkoxy of 1 to 4 carbon atoms, allyloxy, benzyloxy, methoxy-ethoxy, methylthio, methylsulfinyl, methylsulfonyl or methylsulfinylethoxy,
$R_2$ is hydrogen, hydroxyl, methyl, methoxy, ethoxy, fluorine, chlorine, (alkyl of 1 to 4 carbon atoms)-thio, (alkyl of 1 to 4 carbon atoms)-sulfinyl, (alkyl of 1 to 4 carbon atoms)-sulfonyl, dimethylamino or Z-A-O-
where
A is alkylene of 2 to 3 carbon atoms, and
Z is chlorine, hydroxyl, methylthio, ethylthio, methylsulfinyl, ethylsulfinyl, methylsulfonyl, ethylsulfonyl, methylamino, dimethylamino, diethylamino, phenethylamino, N-methyl-phenethylamino or N-methyl-dimethoxyphenethylamino,
$R_3$ is hydrogen or methoxy,
or any two of $R_1$, $R_2$ and $R_3$ together are methylenedioxy, and
$R_5$ is hydrogen, chlorine or methyl,
and non-toxic, pharmacologically acceptable acid addition salts thereof; the compounds as well as the salts are useful as cardiotonics, anticoagulants and for altering the blood pressure.

13 Claims, No Drawings

2-PHENYL-IMIDAZO (4,5-B)PYRIDINES AND SALTS THEREOF

This is a continuation-in-part of copending application Ser. No. 439,362 filed Feb. 4, 1974, now abandoned.

This invention relates to novel 2-phenyl-imidazo[4,5-b]pyridines and non-toxic, pharmacologically acceptable acid addition salts thereof, as well as to methods of preparing these compounds.

More particularly, the present invention relates to a novel class of imidazo pyridine derivatives represented by the isomeric formulas

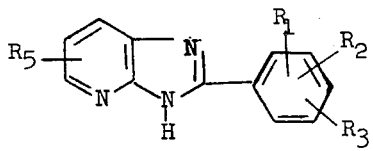

(I)

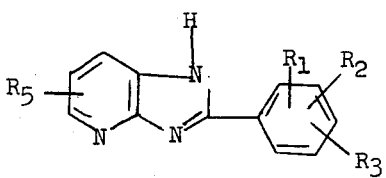

(Ia)

wherein
$R_1$ is hydroxyl, alkoxy of 1 to 4 carbon atoms, allyloxy, benzyloxy, methoxy-ethoxy, methylthio, methylsulfinyl, methylsulfonyl or methylsulfinylethoxy,
$R_2$ is hydrogen, hydroxyl, methyl, methoxy, ethoxy, fluorine, chlorine, (alkyl of 1 to 4 carbon atoms)-thio, (alkyl of 1 to 4 carbon atoms)-sulfinyl, (alkyl of 1 to 4 carbon atoms)-sulfonyl, dimethylamino or Z-A-O
where
A is alkylene of 2 to 3 carbon atoms, and
Z is chlorine, hydroxyl, methylthio, ethylthio, methylsulfinyl, ethylsulfinyl, methylsulfonyl, ethylsulfonyl, methylamino, dimethylamino, diethylamino, phenethylamino, N-methylphenethylamino or N-methyl-dimethoxyphenethylamino,
$R_3$ is hydrogen or methoxy
or any two of $R_1$, $R_2$ and $R_3$ together are methylenedioxy, and
$R_5$ is hydrogen, chlorine or methyl,
and non-toxic, pharmacologically acceptable acid addition salts thereof.

A preferred sub-genus thereunder is constituted by those compounds of formulas I and Ia
wherein
$R_1$ is methoxy, ethoxy, methylthio or methoxyethoxy,
$R_2$ is methyl, methoxy, ethoxy, fluorine, methylthio, ethylthio, methylsulfinyl, ethylsulfinyl, methylsulfonyl, ethylsulfonyl or (alkyl of 1 to 2 carbon atoms)-sulfinyl-(alkoxy of 2 3 carbon atoms) and
$R_3$ and $R_5$ are hydrogen,
and non-toxic, pharmacologically acceptable acid addition salts thereof.

The compounds embraced by formulas I and Ia above may be prepared by the following methods:
By reacting a pyridine of the formula

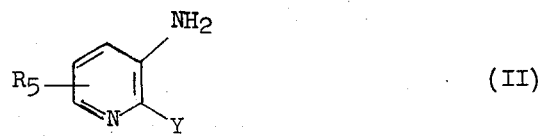

(II)

wherein
$R_5$ has the same meanings as in formulas I and Ia, and
Y is halogen or $NH_2$—,
with a compound of the formula

(III)

wherein
$R_1$, $R_2$ and $R_3$ have the same meanings as in formulas I and Ia, and
X is carboxyl or a functional derivative thereof.

Suitable examples of carboxylic acid derivatives include the nitrile, acid halide, ester, amide, imido acid ester, imido acid thioester, imido acid halide, amidine, thiocarboxylic acid, dithiocarboxylic acid, N-carboxylic acid anhydride or ortho-ester derivative.

The reaction is advantageously carried out in a suitable solvent, such as benzene, pyridine, glycol, toluene, acetone, diethyleneglycol or triethylamine, optionally in the presence of an acid binding agent, such as pyridine or triethylamine, optionally in the presence of a catalytic quantity of an acid such as p-toluenesulfonic acid, or optionally in the presence of a dehydrating agent, such as phosphorus oxychloride or thionyl chloride; and, depending upon the reactivity of X, at temperatures between −20° C and 250° C. The reaction may, however, also be performed in the absence of a solvent.

If X, for example, is a carboxyl or an amide derivative thereof, the reaction is appropriately carried out in the presence of phosphorus oxychloride or thionyl chloride, and optionally in the presence of a tertiary organic base, such as pyridine or triethylamine, preferably at temperatures between −20° C and the boiling point of the solvent used, for example, at 120° C.

If X, for example, is cyano, the reaction is appropriately performed in the presence of a catalytic quantity of an acid, such as p-toluenesulfonic acid preferably at temperatures between 120° and 180° C, for example, 160° C, optionally in the presence of a solvent.

If X, for example, is a thioamide derivative, the reaction is appropriately effected in a solvent, such as glycol, and preferably at temperatures between 100° and 150° C, for example, at 130° C.

If Y is halogen in a compound of the formula II, for example, chlorine, the reaction is carried out via the corresponding amidine, which is cyclized at elevated temperatures for example, at temperatures between 100° and 200° C, optionally without previous isolation.

The compounds embraced by formulas I and Ia above, which contain a reactive halogen, may subsequently be converted into the corresponding amino compound with an amine, and/or the compounds embraced by formulas I and Ia above, which contain reactive hydrogen atoms, may subsequently be alkylated by means of a known alkylating agent in the presence of a base.

The starting compounds used for this process are known from the literature, or they may be prepared according to known processes, as illustrated in the examples below.

The compounds embraced by formulas I and Ia are organic bases and, therefore, form acid addition salts with inorganic or organic acids, by known methods. Examples of non-toxic, pharmacologically acceptable acid addition salts are those formed with hydrochloric acid, hydrobromic acid, sulfuric acid, lactic acid, citric acid, maleic acid, fumaric acid, tartaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

2-(2',4'-Dimethoxyphenyl)-1H-imidazo[4,5-b]pyridine and its hydrochloride 54.5 gm of 2,3-diaminopyridine and 91.1 gm of 2,4-dimethoxybenzoic acid were finely pulverized and added by small amounts to 1500 ml of phosphorus oxychloride while stirring. Afterwards, the mixture was refluxed for 2 hours, then the phosphorus oxychloride was distilled off in vacuo. The residue was triturated with 2000 ml of 2N hydrochloric acid. The obtained solid product was vacuum filtered and recrystallized from water yielding 121 gm, 85% of theory, of the hydrochloride salt, m.p. of 238° C, of the formula

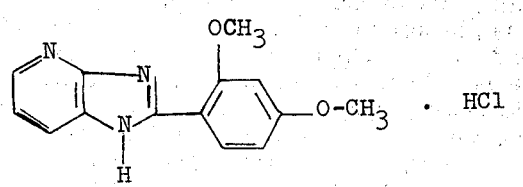

EXAMPLE 2

2-(2',4'-Dimethoxyphenyl)-1H-imidazo[4,5-b]pyridine and its hydrochloride 300 mgm of 2,4-dimethoxybenzoic acid-(4'-chloroanilide) and 110 mgm of 2,3-diaminopyridine were mixed and added by small amounts to 3 ml of phosphorus oxychloride while stirring. Afterwards the mixture was refluxed for 8 hours; then the phosphorus oxychloride was removed in vacuo. The residue was triturated with 2N hydrochloric acid. The obtained solid product was vacuum filtered and recrystallized from water, yielding the hydrochloride salt, m.p. 237° to 238° C.

EXAMPLE 3

2-(3',4'5'-Trimethoxyphenyl)-1H-imidazo[4,5-b]pyridine 3.4 gm of p-toluenesulfonic acid-monohydrate and 15 ml of benzene were heated at 120° C until all of the benzene was evaporated. Subsequently, 1.1 gm of 2,3-diaminopyridine and 2 gm of 3,4,5-trimethoxybenzoic acid nitrile were added, and the mixture was heated for 2 hours at 150° C. After cooling, water was added, and the mixture was extracted with ethyl acetate. The ethyl acetate layers were washed with dilute sodium hydroxide solution, evaporated, and the residue was recrystallized from isopropanol/petroleum ether. The free base, m.p. 226° C, had the formula

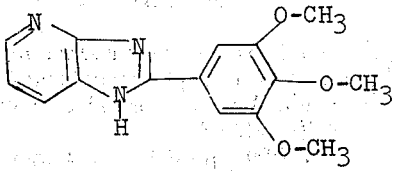

EXAMPLE 4

2-(2',5'-Dimethoxy-phenyl)-1H-imidazo[4,5-b]pyridine a. 2,5-Dimethoxy-thiobenzoic acid morpholide A mixture of 10 gm of 2,5-dimethoxybenzaldehyde, 10 gm of morpholine and 5 gm of sulfur was heated at 130° C for 3.5 hours and subsequently was dissolved in 300 ml of hot ethanol. The product which precipitated upon cooling was recrystallized from ethanol and had a m.p. of 127° C.

b. S-Methyl-2,5-dimethoxy-thiobenzoic acid morpholide iodide 6 gm of 2,5-dimethoxy-thiobenzoic acid morpholide, 6.5 gm of methyl iodide and 30 ml of acetone were refluxed for 8 hours. Subsequently the precipitated solid product was vacuum filtered and washed with ether. The product obtained was not purified.

c. 2-(2',5'-Dimethoxy-phenyl)-1H-imidazo[4,5-b]pyridine 2 gm of S-methyl-2,5-dimethoxy-thiobenzoic acid morpholide iodide and 1.1 gm of 2,3-diaminopyridine were heated in 30 ml of glycol for 40 minutes at 130° C. Subsequently the mixture was poured into ice water, vacuum filtered and recrystallized from ethanol/water. The free base had a m.p. of 235° C.

EXAMPLE 5

2-(4'-Hydroxy-phenyl)-1H-imidazo[4,5-b]pyridine a. 4-Hydroxy-thiobenzoic acid morpholide Using a procedure analogous to that described in Example 4a, 4-hydroxy-thiobenzoic acid morpholide was prepared from 12.2 gm of 4-hydroxy-benzaldehyde, 16 gm of morpholine and 3.2 gm of sulfur and had a m.p. of 205° C.

b. S-Methyl-4-hydroxy-thiobenzoic acid morpholide iodide

Using a procedure analogous to that described in Example 4b, S-methyl-4-hydroxy-thiobenzoic acid morpholide iodide was prepared from 14.4 gm of 4-hydroxy-thiobenzoic acid-morpholide and 2.1 gm of methyliodide in 100 ml of acetone, and had a m.p. of 181° C.

c. 2-(4'-Hydroxy-phenyl)-1H-imidazo[4,5-b]pyridine 1.84 gm of S-methyl-4-hydroxy-thiobenzoic acid morpholide iodide were heated for 20 minutes at 130° C with 1.1 gm of 2,3-diaminopyridine in 30 ml of glycol. The product precipitated upon cooling was dissolved in sodium hydroxide solution and reprecipitated with an acid, yielding the free base of the formula

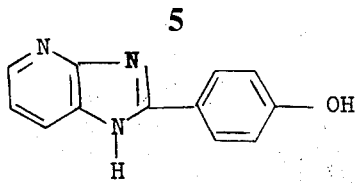

| Analysis: | | | |
|---|---|---|---|
| Calculated: | C 65.87% | H 5.13% | N 16.46% |
| Found | 65.90% | 5.16% | 16.47% |

EXAMPLE 6

2-[p-Methoxy-o-(3'-chloropropoxy)-phenyl]-1H-imidazo[4,5-b]pyridine and its hydrochloride a. 4-Methoxy-2-(3'chloro-propoxy)-benzoic acid morpholide 21.9 gm of 2-hydroxy-4-methoxy-benzoic acid morpholide were dissolved in 200 ml of dimethylformamide, and 11.2 gm of potassium tert. butylate were added. After all the product had dissolved, 50 gm of 1-chloro-3-bromo-propane were added, and the mixture was heated for 2 hours at 130° C. Subsequently the mixture was evaporated in vacuo; and the residue was dissolved in ethyl acetate. The solution was washed with sodium hydroxide solution, water and evaporated.

b. 2-[p-Methoxy-o-(3'-chloropropoxy)-phenyl]-1H-imidazo[4,5-b]pyridine hydrochloride 20 gm of p-methoxy-o-(3-chloro-propoxy)-benzoic acid morpholide, 7 gm of 2,3-diamino-pyridine and 170 ml of phosphorus oxychloride were refluxed for 2 hours. After evaporation of the phosphorus oxychloride, the residue was mixed with water, neutralized with sodium hydroxide solution and extracted with ethyl acetate. The hydrochloride which precipitated upon addition of ethereal hydrochloric acid, had a m.p. of 198° C (decomp.) and the formula

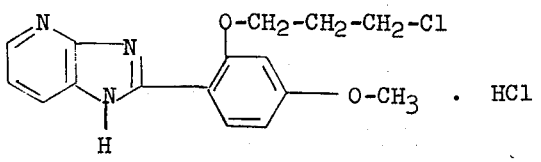

EXAMPLE 7

2-[p-Methoxy-o-(2'-chloroethoxy)-phenyl]-1H-imidazo[4,5-b]pyridine and its hydrochloride a. 4-Methoxy-2-(2'-hydroxy-ethoxy)-benzoic acid morpholide 23.7 gm of 2-hydroxy-4-methoxy-benzoic acid morpholide, 33.6 gm of potassium tert. butylate and 37.4 gm of ethylenebromohydrin were heated in 100 ml of dimethylformamide for 6 hours at 120° C. After evaporation in vacuo, the residue was dissolved in chloroform; and the solution was washed with sodium hydroxide solution, water and evaporated.

b. 2-[p-Methoxy-o-(2'-chloroethoxy)-phenyl]-1H imidazo[4,5-b]pyridine and its hydrochloride 2.8 gm of 4-methoxy-2-(2'-hydroxy-ethoxy)-benzoic acid morpholide, 1.1 gm of 2,3-diaminopyridine and 20 ml of phosphorus oxychloride were refluxed for 2 hours. After evaporation, water was added; the mixture was neutralized and extracted with ethyl acetate. Upon the addition of ethereal hydrochloric acid, the hydrochloride was precipitated from the organic layer, m.p. 100° C (decomp.).

EXAMPLE 8

2-[4'-Methoxy-2'-(3''-dimethylamino-propoxy)-phenyl]-1H-imidazo[4,5-b]pyridine and its hydrochloride 1.8 gm of 2-[4'-methoxy-2'-(3''-chloropropoxy)-phenyl]-1H-imidazo[4,5-b]pyridine hydrochloride and 20 ml of saturated dimethylamine solution in ethanol were heated for 8 hours in a closed vessel at 100° C. Subsequently, the mixture was evaporated in vacuo, and the residue was recrystallized from isopropanol, yielding the hydrochloride, m.p. 209° to 210° C, of the formula

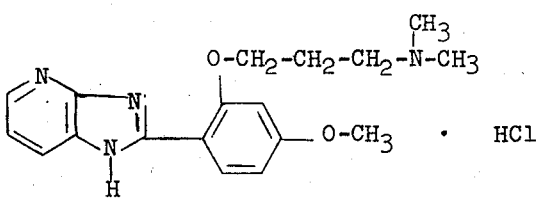

EXAMPLE 9

2-[4'-Methoxy-2'-(3''-dimethylamino-propoxy)-phenyl]-1H-imidazo-[4,5-b]pyridine and its dihydrochloride 1.64 gm of 4-methoxy-2-(3'-dimethylamino-propoxy)-thiobenzoic acid-morpholide were dissolved in a mixture of 17 ml of glacial acetic acid and 3 ml of acetic anhydride. Then 1 ml of dimethylsulfate was added, and the mixture was heated on a steam bath for 1 hour. Subsequently, the mixture was evaporated in vacuo. The obtained crude S-methyl-4-methoxy-2-(3'-dimethylamino-propoxy)-thiobenzoic acid-morpholide-methyl sulfate was dissolved in 13 ml of glycol. Then 0.7 gm of 2,3-diaminopyridine was added, and the mixture was heated for 2 hours at 160° C. Subsequently, the mixture was poured into 50 ml of water; 5 ml of concentrated ammonia were added; and the mixture was extracted with ethyl acetate. The ethyl acetate layers were evaporated; the residue was dissolved in ethanol; ethereal hydrochloric acid was added and the acidic solution was again evaporated. The residue crystallized upon trituration with toluene and a small quantity of ethanol. The product was vacuum filtered, and recrystallized from isopropanol, yielding the dihydrochloride hydrate, m.p. 228°–235° C (decomp.).

EXAMPLE 10

2-(2',4'-Dimethoxy-phenyl)-1H-imidazo[4,5-b]pyridine and its hydrochloride 2.2 gm of 2,3-diaminopyridine, 6.8 gm of the imide chloride of 2,4-dimethoxy-benzoic acid-morpholide and 12 ml of triethylamine were heated for 0.5 hour at 120° C in 10 ml of diethyleneglycol-dimethylether. After cooling, water was added, the reaction mixture was extracted with chloroform, and the chloroform layer was extracted with 2N sodium hydroxide solution. The yellow hydrochloride precipitated from the acidic solution was converted into the base with ammonia, which was purified by column chromatography. The hydrochloride, m.p. 237°–238° C, was reprecipitated from acetone with ethereal hydrochloric acid.

EXAMPLE 11

2-(2′-Methoxyphenyl)-1H-imidazo[4,5-b]pyridine and its hydrochloride a. 2-Methoxy-thiobenzoic acid morpholide 34 gm of 2-methoxybenzaldehyde, 16 gm of sulfur and 32.6 gm of morpholine were heated for 3 hours at 120° C. The reaction mixture thus obtained was dissolved in ethanol, filtered, cooled and the precipitated yellow crystals were vacuum filtered. The yield was 54.1 gm (91% of theory), and the m.p. was 80°–82° C.

b. 2-Methoxy-thiobenzoic acid morpholide methoiodide 47.4 gm of 2-methoxy-thiobenzoic acid morpholide were refluxed for 1 hour in 150 ml of acetone with 25 ml of methyl iodide, and the yellow crystals precipitated which upon cooling were vacuum filtered. The yield was 64.4 gm (85% of theory), and the m.p. was 162°–164°C.

c. 2-(o-Methoxyphenyl)-1H-imidazo[4,5-b]pyridine 19 gm of 2-methoxy-thiobenzoic acid morpholide methoiodide and 8.7 gm of 2,3-diaminopyridine were heated for 3 hours at 120° C in 70 ml of glycol. After cooling, water was added, the mixture was made alkaline with ammonia and extracted with chloroform. The organic layer was washed with water and subsequently 2N hydrochloric acid was added. The precipitated product was vacuum filtered; the base was set free with ammonia, taken up in chloroform and purified over a silicagel column. The colorless hydrochloride, m.p. 233°–234° C was obtained from acetone upon addition of ethereal hydrochloric acid.

EXAMPLE 12

Using a procedure analogous to that described in Example 11, 2-(2′-methoxyphenyl)-3-methyl-3H-imidazo[4,5-b]pyridine, was prepared from 2-methylamino-3-amino-pyridine and 2-methoxy-thiobenzoic acid-morpholide methoiodide. Its hydrochloride had a melting point of 208°–210° C.

EXAMPLE 13

Using a procedure analogous to that described in Example 11, 2-[2′-(2′′-methoxy-ethoxy)-phenyl]-1H-imidazo[4,5-b]pyridine, was prepared from 2-(2-methoxy-ethoxy)-thiobenzoic acid morpholide methoiodide and 2,3-diamino pyridine. Its hydrochloride, m.p. 170°–172° C, had the formula

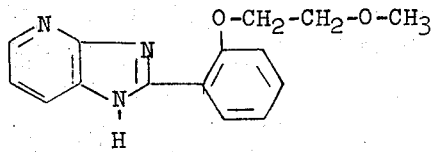

EXAMPLE 14

Using a procedure analogous to that described in Example 11, 2-(p-methoxyphenyl)-1H-imidazo[4,5-b]pyridine, was prepared from 4-methoxy-thiobenzoic acid morpholide methoiodide, m.p. 142°–144° C, and 2,3-diamino-pyridine. Its hydrochloride had a melting point of 243°–245° C.

EXAMPLE 15

Using a procedure analogous to that described in Example 11, 2-(3′-methoxy-4′-hydroxy-phenyl)-1H-imidazo[4,5-b]pyridine, was prepared from 3-methoxy-4-hydroxy-thiobenzoic acid morpholide methoiodide, m.p. 178°–180° C, and 2,3-diamino-pyridine. Its hydrochloride had a melting point of 251°–254° C.

EXAMPLE 16

Using a procedure analogous to that described in Example 11, 2-(2′,3′-dimethoxy-phenyl)-1H-imidazo[4,5-b]pyridine, was prepared from 2,3-dimethoxy-thiobenzoic acid morpholide methoiodide, m.p. 138°–140° C and 2,3-diamino-pyridine. Its hydrochloride had a melting point of 270°–272° C.

EXAMPLE 17

Using a procedure analogous to that described in Example 11, 2-(2′hydroxy-4′-methoxy-phenyl)-1H-imidazo[4,5-b]pyridine, m.p. 292°–293° C, was prepared from 2-hydroxy-4-methoxy-thiobenzoic acid morpholide methoiodide, m.p. 180°–181° C, and 2,3-diamino-pyridine. Its hydrochloride had a melting point of 190°–192° C (decomp.).

EXAMPLE 18

Using a procedure analogous to that described in Example 11, 2-(2′,4′-dimethoxy-phenyl)-1H-imidazo[4,5-b]pyridine, was prepared from 2,4-dimethoxy-thiobenzoic acid morpholide methoiodide, m.p. 138°–140° C (decomp.), and 2,3-diamino-pyridine. Its hydrochloride had a melting point of 238° C (from methanol).

EXAMPLE 19

Using a procedure analogous to that described in Example 18, 2-(2′,4′-dimethoxy-phenyl)-6-methyl-1H-imidazo[4,5-b]pyridine, was prepared from 2,3-diamino-5-methyl-pyridine and 2,4-dimethoxy-thiobenzoic acid morpholide methoiodide. Its hydrochloride, m.p. 260°–261° C, had the formula

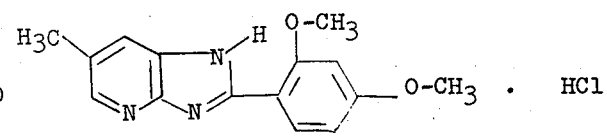

EXAMPLE 20

Using a procedure analogous to that described in Example 18, 2-(2′,4′-dimethoxy-phenyl)-7-methyl-1H-imidazo[4,5-b]pyridine, was prepared from 2,3-diamino-4-methyl-pyridine and 2,4-dimethoxy-thiobenzoic acid morpholide methoiodide. Its hydrochloride had a melting point of 230°–231° C.

EXAMPLE 21

Using a procedure analogous to that described in Example 18, 2-(2′,4′-dimethoxy-phenyl)-5-methyl-1H-imidazo[4,5-b]pyridine, was prepared from 2,3- diamino-6-methyl-pyridine and 2,4-dimethoxy-thiobenzoic acid morpholide methoiodide. Its hydrochloride had a melting point of 245°–246° C.

EXAMPLE 22

Using a procedure analogous to that described in Example 18, 2-(2',4'-dimethoxy-phenyl)-6-chloro-1H-imidazo[4,5-b]pyridine, was prepared from 2,3-diamino-5-chloro-pyridine and 2,4-dimethoxy-thiobenzoic acid morpholide methoiodide. Its hydrochloride had a melting point of 253°–255° C.

EXAMPLE 23

Using a procedure analogous to that described in Example 11, 2-(2'-ethoxy-4'-methoxy-phenyl)-1H-imidazo[4,5-b]pyridine, was prepared from 2-ethoxy-4-methoxy-thiobenzoic acid morpholide methoiodide, m.p. 152°–154° C, and 2,3-diamino-pyridine. Its hydrochloride had a melting point of 228°–230° C.

EXAMPLE 24

Using a procedure analogous to that described in Example 11, 2-(2'methoxy-4'-ethoxy-phenyl)-1H-imidazo[4,5-b]pyridine, was prepared from 2-methoxy-4-ethoxy-thiobenzoic acid morpholide methoiodide and and 2,3-diamino-pyridine. Its hydrochloride had a melting point of 224°–225° C (from methanol).

EXAMPLE 25

Using a procedure analogous to that described in Example 11, 2-(2',4'-diethoxy-phenyl)-1H-imidazo[4,5-b]pyridine, was prepared from 2,4-diethoxy-thiobenzoic acid morpholide methoiodide and 2,3-diamino-pyridine. Its hydrochloride had a melting point of 224°–226° C.

EXAMPLE 26

Using a procedure analogous to that described in Example 11, 2-[2'(β-hydroxy-ethoxy)-4'-methoxy-phenyl]-1H-imidazo[4,5-b]pyridine, was prepared from 2-(β-hydroxy-ethoxy)-4-methoxy-thiobenzoic acid morpholide methoiodide and 2,3-diamino-pyridine. Its hydrochloride, m.p. 237°–239° C, had the formula

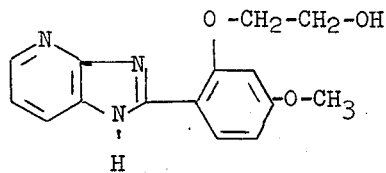

EXAMPLE 27

Using a procedure analogous to that described in Example 11, 2-[o-(3'-hydroxy-propoxy)-p-methoxy-phenyl]-1H-imidazo[4,5-b]pyridine, was prepared from 2-(3-hydroxy-propoxy)-4-methoxy-thiobenzoic acid morpholide methoiodide and 2,3-diamino-pyridine. Its hydrochloride had a melting point of 170° C (sintering).

EXAMPLE 28

Using a procedure analogous to that described in Example 11, 2-[2'-(β-methoxy-ethoxy)-4'-methoxy-phenyl]-1H-imidazo[4,5-b]-pyridine, was prepared from 2-(β-methoxy-ethoxy)-4-methoxy-thiobenzoic acid morpholide methoiodide and 2,3-diamino-pyridine. Its hydrochloride had a melting point of 191°–193° C.

EXAMPLE 29

2-[2'-Methoxy-4'-(β-methylmercapto-ethoxy)-phenyl]-1H-imidazo[4,5-b]pyridine and its hydrochloride a. 4-(β-Methylmercapto-ethoxy)-2-hydroxy-benzaldehyde 12 gm of 2,4-dihydroxy-benzaldehyde and 9.6 gm of potassium tert. butylate were dissolved in 50 ml of ethyleneglycol monomethyl ether. 9.6 gm of methylmercaptoethyl chloride were added, and the reaction mixture was stirred for 8 hours at 80° C (bath temperature). After removing the solvent, the residue was dissolved in a dilute solution of sodium hydroxide, the mixture was extracted twice with chloroform, and the aqueous alkaline solution was separated, acidified and extracted with chloroform. The organic phase was dried and evaporated. The residue was purified by column chromatography (silicagel). The oil thus obtained was used directly in the next step.

b. 4-β-Methylmercapto-ethoxy)-2-methoxy-benzaldehyde 9.7 gm of 4-(β-methylmercapto-ethoxy)-2-hydroxy-benzaldehyde were dissolved in ethanol together with 6.7 gm of potassium tert. butylate; 4.3 ml of dimethyl-sulfate were added, and the mixture was refluxed for 3 hours. Then, again 1 ml of dimethyl-sulfate was added, and the mixture was heated for a further hour. After the ethanol had been distilled off, the residue was dissolved in water/chloroform, and 2N sodium hydroxide solution was added. The chloroform layer was separated, washed with water, dried and evaporated. The compound had a melting point of 99°–100° C (from cyclohexane).

c. Using a procedure analogous to that described in Example 11a, 4-(β-methylmercapto-ethoxy)-2-methoxy-thiobenzoic acid morpholide, m.p. 131°–132° C (from ethanol), was prepared from 4-(β-methylmercapto-ethoxy)-2-methoxy-benzaldehyde.

d. 2-[2'-Methoxy-4'(β-methylmercapto-ethoxy)-phenyl]-1H-imidazo[4,5-b]pyridine 5.4 gm of 4-(β-methylmercapto-ethoxy)-2-methoxy-thiobenzoic acid morpholide were refluxed for 1.5 hours together with 1.2 ml of methyl iodide in 50 ml of acetone. After cooling, the solvent was removed and the obtained syrupy methoiodide was heated with 3.6 gm of 2,3-diamino-pyridine in 20 ml of glycol for 1.5 hours at 120° C. The mixture was diluted with water and extracted with chloroform. Subsequently, 2N hydrochloric acid was added to the organic layer, and the yellow precipitate was vacuum filtered. The hydrochloride, m.p. 197°–199° C (from methanol), had the formula

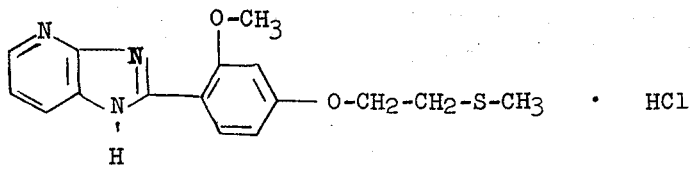

EXAMPLE 30

Using a procedure analogous to that described in Example 29, 2-[2'-methoxy-4'-(2''-ethylmercapto-ethoxy)-phenyl]-1H-imidazo[4,5-b]pyridine, was prepared from 4-(2-ethylmercapto-ethoxy)-2-methoxy-thiobenzoic acid morpholide and 2,3-diamino-pyridine. The purification of the final product was effected by chromatography over silicagel, and the precipitation of the hydrochloride was effected by dissolving the base in acetone and adding an excess of ethereal hydrochloric acid. The hydrochloride had a melting point of 195°–196° C.

EXAMPLE 31

Using a procedure analogous to that described in Example 29, 2-[2'-methoxy-4'-(3''-methylmarcapto-propoxy)-phenyl]-1H-imidazo[4,5-b]pyridine, was prepared from 4-(3'-methylmercapto-propoxy)-2-methoxy-thiobenzoic acid morpholide and 2,3-diamono-pyridine. Its hydrochloride had a melting point of 189°–191° C (decomp.).

EXAMPLE 32

Using a procedure analogous to that described in Example 29, 2-[2'-methoxy-4'(3''-ethylmercapto-propoxy)-phenyl]-1H-imidazo[4,5-b]pyridine, was prepared from 4-(3'-ethylmercapto-propoxy)-2-methoxy-thiobenzoic acid morpholide and 2,3-diamono-pyridine. Its hydrochloride had a melting point of 183°–185° C (decomp.).

EXAMPLE 33

Using a procedure analogous to that described in Example 29, 2-[2'-(2''-methylmercapto-ethoxy)-4'-methoxy-phenyl]-1H-imidazo[4,5-d]pyridine, was prepared from 2-(2'-methylmercapto-ethoxy)-4-methoxy-thiobenzoic acid morpholide and 2,3-diamino-pyridine. Its hydrochloride had a melting point of 204°–206° C (decomp.).

EXAMPLE 34

Using a procedure analogous to that described in Example 29, 2-[2'-(2''-ethylmercapto-ethoxy)-4'-methoxy-phenyl]-1H-imidazo[4,5-b]pyridine, was prepared from 2-(2'-ethylmercapto-ethoxy)-4-methoxy-thiobenzoic acid morpholide and 2,3-diamino-pyridine. Its hydrochloride had a melting point of 193°–195° C.

EXAMPLE 35

Using a procedure analogous to that described in Example 29, 2-[2'-(3''-methylmercapto-propoxy)-4'-methoxy-phenyl]-1H-imidazo[4,5-b]pyridine, was prepared from 2-(3'-methylmercapto-propoxy)-4-methoxy-thiobenzoic acid morpholide and 2,3-diamino-Pyridine. Its hydrochloride had a melting point of 191°–193° C.

EXAMPLE 36

Using a procedure analogous to that described in Example 29, 2-[2'-(3''-ethylmercapto-propoxy)-4'-methoxy-phenyl]-1H-imidazo[4,5-b]pyridine, was prepared from 2-(3'-ethylmercapto-propoxy)-4-methoxy-thiobenzoic acid morpholide and 2,3-diamino-pyridine. Its hydrochloride had a melting point of 187°–189° C.

EXAMPLE 37

Using a procedure analogous to that described in Example 11, 2-(2',3',4'-trimethoxy-phenyl)-1H-imidazo[4,5-b]pyridine, was prepared from 2,3,4-trimethoxy-thiobenzoic acid morpholide methoiodide, m.p. 147°–150° C, and 2,3-diamino-pyridine. Its hydrochloride had a melting point of 231°–233° C (decomp.).

EXAMPLE 38

Using a procedure analogous to that described in Example 11, 2-(2'-methoxy-3',4'-methylenedioxy-phenyl)-1H-imidazo[4,5-b]pyridine, was prepared from 2-methoxy-3,4-methylenedioxy-thiobenzoic acid morpholide methoiodide, m.p. 109°–111° C, and 2,3-diamino-pyridine. Its hydrochloride, m.p. 266°–268° C, had the formula

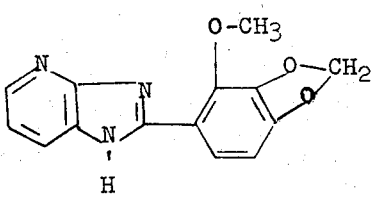

EXAMPLE 39

Using a procedure analogous to that described in Example 11, 2-(2',4'-dimethoxy-3'-hydroxy-phenyl)-1H-imidazo[4,5-b]pyridine, was prepared from 2,4-dimethoxy-3-hydroxy-thiobenzoic acid morpholide methoiodide and 2,3-diamino-pyridine. Its hydrochloride had a melting point of 115°–118° C.

EXAMPLE 40

Using a procedure analogous to that described in Example 11, 2-(2'-methoxy-4'-chloro-phenyl)-1H-imidazo[4,5-b]pyridine, was prepared from 2-methoxy-4-chloro-thiobenzoic acid morpholide methoiodide and 2,3-diamino-pyridine. Its hydrochloride had a melting point of 302°–305° C.

EXAMPLE 41

Using a procedure analogous to that described in Example 11, 2-(2'-methoxy-4'-methyl-phenyl)-1H-imidazo[4,5-b]pyridine, was prepared from 2-methoxy-4-methyl-thiobenzoic acid-thiomorpholide and 2,3-diaminopyridine. Its hydrochloride had a melting point of 256° C (decomp.).

EXAMPLE 42

Using a procedure analogous to that described in Example 11, 2-(2'-ethoxy-4'-methyl-phenyl)-1H-imidazo[4,5-b]pyridine, was prepared from 2-ethoxy-4-methyl-thiobenzoic acid morpholide methoiodide, m.p. 142°–144° C, and 2,3-diamino-pyridine. Its hydrochloride had a melting point of 224°–225° C (decomp.).

EXAMPLE 43

Using a procedure analogous to that described in Example 11, 2-(2'-methoxy-4'-methylmercapto-phenyl)-1H-imidazo[4,5-b]pyridine, was prepared from 2-hydroxy-4-methylmercapto-benzoic acid morpholide, m.p. 124°–129° C, and 2,3-diamino-pyridine. Its hydrochloride had a melting point of 232°–234° C.

EXAMPLE 44

Using a procedure analogous to that described in Example 11, 2-(2'-methoxy-5'-methylmercapto-phenyl)-1H-imidazo[4,5-b]pyridine, was prepared from 2-methoxy-5-methylmercapto-benzoic acid morpholide, m.p. 106°–108° C, and 2,3-diamino-pyridine. Its hydrochloride had a melting point of 247°–248° C.

EXAMPLE 45

Using a procedure analogous to that described in Example 11, 2-(2'-methoxy-4'-ethylmercapto-phenyl)-1H-imidazo[4,5-b]pyridine, was prepared from 2-methoxy-4-ethylmercapto-benzoic acid morpholide and 2,3-diamino-pyridine. Its hydrochloride had a melting point of 215°–217° C.

EXAMPLE 46

Using a procedure analogous to that described in Example 11, 2-(2'-methylmercapto-phenyl)-1H-imidazo[4,5-b]pyridine, was prepared from 2-methylmercapto-thiobenzoic acid morpholide methoiodide and 2,3-diamino-pyridine. Its hydrochloride had a melting point of 185°–187° C.

EXAMPLE 47

Using a procedure analogous to that described in Example 11, 2-(2',4'-bismethylmercapto-phenyl)-1H-imidazo[4,5-b]pyridine, was prepared from 2,4-bis-methylmercapto-thiobenzoic acid morpholide methoiodide and 2,3-diamino-pyridine. Its hydrochloride had a melting point of 249°–250° C.

EXAMPLE 48

Using a procedure analogous to that described in Example 11, 2-[2'-(β-methylmercapto-ethoxy-4'-methylmercapto-phenyl]-1H-imidazo[4,5-b]pyridine, was prepared from 2-(β-methylmercapto-ethoxy)-4methylmercapto-thiobenzoic acid morpholide methoiodide and 2,3-diamino-pyridine. Its hydrochloride had a melting point of 180°–132° C.

EXAMPLE 49

Using a procedure analogous to that described in Example 11, 2-[2'-β-diethylamino-ethoxy)-4'-methyl-phenyl]-1H-imidazo[4,5-]pyridine, was prepared from 2-(β-diethylamino-ethoxy)-4-methyl-thiobenzoic acid morpholide methoiodide hydrochloride and 2,3-diamino-pyridine. Its hydrochloride, m.p. 221°–223° C, had the formula

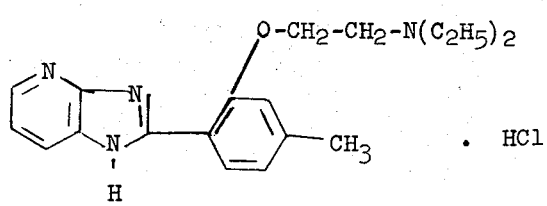

EXAMPLE 50

2-(2'-Allyloxy-4'-methoxy-phenyl)-1H-imidazo[4,5-b]pyridine and its hydrochloride 16.5 gm of 2-allyloxy-4-methoxy-benzoic acid morpholide and 7.1 gm of 2,3-diamono-pyridine were intimately mixed and pulverized, and 30 ml of phosphorus oxychloride were added dropwise while stirring. Subsequently, the reaction mixture was refluxed for 3 hours, the phosphorus oxychloride was removed, and the residue was decomposed with ice water. The solution, which had been made alkaline with ammonia, was extracted with chloroform, and the organic solution was extracted with 2N hydrochloric acid. The aqueous phase was made alkaline with ammonia, extracted with chloroform, and the chloroform solution was dried, treated with activated charcoal/bleaching earth, filtered and evaporated. The residue was dissolved in acetone. The light yellow colored hydrochloride, m.p. 189°–191° C, was precipitated upon addition of ethereal hydrochloric acid and had the formula

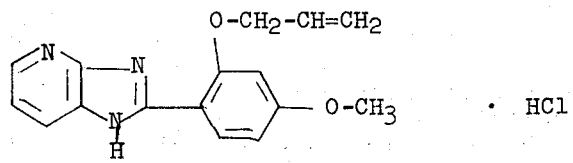

EXAMPLE 51

2-(2',4',5'-Trimethoxy-phenyl)-1H-imidazo[4,5-b]pyridine and its hydrochloride a. 2-(2',4',5'-Trimethoxy-phenyl)-1,3-dithiolanium iodide 50 gm of 1,2,4-trimethoxybenzene and 150 gm of 2-methylmercapto-1,3-dithiolanium methosulfate were stirred in 600 ml of glacial acetic acid for 4 hours at 70° C bath temperature. Subsequently, the solvent was removed, and the residue was dissolved in a mixture of chloroform and water. Upon adding an excess of potassium iodide solution to the aqueous layer, the product precipitated out as orange-colored crystals.

b. 2-(2',4',5'-Trimethoxy-phenyl)-1H-imidazo[4,5-b]pyridine and its hydrochloride 3.8 gm of 2-(2',4',5'-trimethoxy-phenyl)-1,3-dithiolanium iodide and 2.2 gm of 2,3-diamino-pyridine were heated for 10 minutes in 40 ml of glycol at 200° C. After cooling, the mixture was extracted with ether and then with chloroform. The chloroform layer was extracted with 2N hydrochloric acid. The precipitated yellow hydrochloride, m.p. 278°–280° C, was vacuum filtered and recrystallized from glycol.

EXAMPLE 52

2-(2',4',6'-Trimethoxy-phenyl)-1H-imidazo[4,5-b]pyridine and its hydrochloride a. 2-(2',4',6'-Trimethoxy-phenyl)-1,3-dithiolanium iodide 33.6 gm of phloroglucinol trimethylether and 105 gm of 2-methylmercapto-1,3-dithiolanium methosulfate were heated at 75° C for 6 hours in 200 ml of glacial acetic acid. After standing overnight the crystals which precipitated were vacuum filtered, dissolved in water and the iodide, m.p. 153°–154° C, was precipitated upon addition of potassium iodide solution.

b. 2-(2',4',6'-Trimethoxy-phenyl)-1H-imidazo[4,5-b]pyridine and its hydrochloride 4 gm of 2-(2',4',6'-trimethoxy-phenyl)-1,3-dithiolanium iodide, 2.2 gm of 2,3-diamino-pyridine and 5 gm of lead acetate were heated for 10 minutes in 75 ml of glycol. Subsequently, the precipitated lead salt was filtered off, and the filtrate was diluted with water and the precipitated product was vacuum filtered. After dissolving in methanolic hydrochloric acid, the salt was purified on a silicagel column (eluant: chlorform:methanol = 9:1) and had a melting point of 241°–244° C (from ethanol).

EXAMPLE 53

Using a procedure analogous to that described in Example 52, 2-(2',4'-dihydroxy-phenyl)-1H-imidazo[4,5-d]pyridine, was prepared from 3-hydroxy-4-[1',3'-dithiacyclopentylidene-(2')]-cyclohexadiene-(2,5)-one-(1) and 2,3-diamino-pyridine. Its hydrochloride had a melting point of 298°–301° C.

EXAMPLE 54

Using a procedure analogous to that described in Example 52, 2-(4'-dimethylamino-phenyl)-1H-imidazo[4,5-b]pyridine, was prepared from 2-(4'-dimethylamino-phenyl)-1,3-dithiolanium iodide and 2,3-diamino-pyridine in n-propanol. Its hydrochloride, m.p. 337°–339° C, had the formula

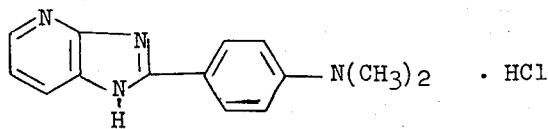

EXAMPLE 55

2-(2'-Methoxy-4'-dimethylamino-phenyl)-1H-imidazo[4,5-b]pyridine and its hydrochloride a. 2-(2'-Methoxy-4'-dimethylamino-phenyl)-1,3-dithiolanium iodide 22.6 gm of 3-dimethylamino-anisole, 43.2 gm of 2-methylmercapto-1,3-dithiolanium methosulfate, 150 ml of glacial acetic acid and 22.5 ml of pyridine were refluxed for ½ hour. After cooling, the mixture was poured into an aqueous potassium iodide solution. The precipitated product was vacuum filtered and dried and had a melting point of 189°–195° C (from dimethylformamide).

b. Using a procedure analogous to that described in Example 25, 2-(2'-methoxy-4-dimethylamino-phenyl)-1H-imidazo[4,5-b]pyridine, was prepared from 2-(2'-methoxy-4'-dimethylamino-phenyl)-1,3-dithiolanium iodide and 2,3-diamino-pyridine. Its hydrochloride had a melting point of 258°–260° C (from methanol).

EXAMPLE 56

2-(2'-Methylsulfinyl-phenyl)-1H-imidazo[4,5-b]pyridine and its hydrochloride 1.35 gm of 2-(2'-methylmercapto-phenyl)-1H-imidazo[4,5-b]pyridine were dissolved in 20 ml of glacial acetic acid, and 0.64 gm of 30% hydrogen peroxide dissolved in 5 ml of glacial acetic acid were added dropwise. After standing overnight, the mixture was diluted with water, neutralized with sodium bicarbonate and the precipitated product was vacuum filtered and dried. Upon the addition of ethereal hydrochloric acid to a methanolic solution of the free base, 2-(2'-methylsulfinyl-phenyl)-1H-imidazo[4,5-b]pyridine, the colorless hydrochloride, m.p. 205°–210° C, having the formula

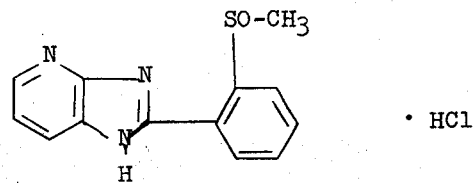

was obtained.

EXAMPLE 57

2-(2'-Methylsulfonyl-phenyl)-1H-imidazo[4,5-b]pyridine and its hydrochloride 450 mgm of 2-(2'-methylmercapto-phenyl)-1H-imidazo[4,5-b]pyridine hydrochloride and 370 mgm of 30% hydrogen peroxide were heated for 3 hours at 70° C in 20 ml of glacial acetic acid. After evaportion, and triturating the residue with petroleum ether, the desired product, m.p. 250°–262° C (from isopropanol), having the formula

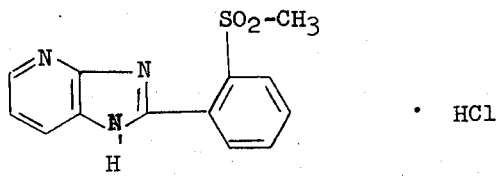

crystallized out.

EXAMPLE 58

2-[2'-(β-Methylsulfinyl-ethoxy)-phenyl]-1H-imidazo[4,5-b]pyridine and its hydrochloride a. Using a procedure analogous to that described in Example 11, 2-[2'-(β-methylmercapto-ethoxy)-phenyl]-1H-imidazo[4,5-b]pyridine, was prepared from 2-(β-methylmercapto-ethoxyl)-thiobenzoic acid morpholide methoiodide and 2,3-diamino-pyridine. Its hydrochloride had a melting point of 138°–140° C.

b. 2-[2'-(β-Methylsulfinyl-ethoxy)-phenyl]-1H-imidazo[4,5-b]pyridine and its hydrochloride 4.3 gm of 2-[2'-(β-methylmercapto-ethoxy)-phenyl]-1H-imidazo[4,5-b]pyridine hydrochloride and 1.5 gm of 30% hydrogen peroxide were stirred for 2 hours at room temperature in 100 ml of glacial acetic acid. After standing overnight, the mixture was diluted with water, neutralized with sodium bicarbonate and extracted with chloroform. The chloroform layer was evaporated, and the residue was dissolved in acetone. The hydrochloride, m.p. 163°–165° C, precipitated upon addition of methanolic hydrochloric acid and had the formula

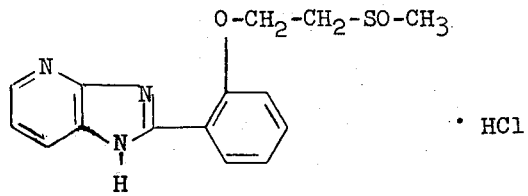

EXAMPLE 59

Using a procedure analogous to that described in Example 58b, 2-[2'-(β-methylsulfinyl-ethoxy)-4'-methoxyphenyl]-1H-imidazo[4,5-b]pyridine, was prepared from 2-[2'-(β-methylmercapto-ethoxy)-4'-methoxy-phenyl]-1H-imidazo[4,5-b]pyridine. Its hydrochloride had a melting point of 231°–232° C.

EXAMPLE 60

Using a procedure analogous to that described in Example 58b, 2-[2'-(β-ethylsulfinyl-ethoxy)-4'-methoxy-phenyl]-1H-imidazo[4,5-b]pyridine, was prepared from 2-[2'-(β-ethylmercapto-ethoxy)-4'-methoxy-phenyl]-1H-imidazo[4,5-b]pyridine. Its hydrochloride had a melting point of 188°–190° C.

EXAMPLE 61

Using a procedure analogous to that described in Example 58b, 2-[2'-(3''-methylsulfinyl-propoxy)-4'-methoxyphenyl]-1H-imidazo[4,5-b]pyridine, was prepared from 2-[2'-(3''-methylmercapto-propoxy)-4'-methoxy-phenyl]-1H-imidazo[4,5-b]pyridine hydrochloride. Its hydrochloride had a melting point of 132°–133° C.

EXAMPLE 62

Using a procedure analogous to that described in Example 58b, 2-[2'-(3''-ethylsulfinyl-propoxy)-4'-methoxyphenyl]-1H-imidazo[4,5-b]pyridine, was prepared from 2-[2'-(3''-ethylmercapto-propoxy)-4'-methoxy-phenyl]-1H-imidazo[4,5-b]pyridine hydrochloride. Its hydrochloride had a melting point of 126°–127° C.

EXAMPLE 63

2-(2'-Methoxy-4'-methylsulfinyl-phenyl)-1H-imidazo[4,5-b]pyridine and its hydrochloride 6.6 gm of 2-(2'-methoxy-4'-methylmercapto-phenyl)-1H-imidazo[4,5-b]pyridine were dissolved in 100 ml of chloroform. A solution of 2.96 gm of 3-chloro-perbenzoic acid in 600 ml of chloroform was added dropwise at −15° to −20°C over a period of 5 hours. Subsequently, the mixture was extracted with a dilute solution of sodium carbonate; the chloroform layer was dried and evaporated. The residue was purified on a silicagel column (eluant:chloroform/methanol = 9:1). Upon addition of ethereal hydrochloric acid to a methanolic solution of the base the yellow hydrochloride, m.p. 154°–155° C, was obtained.

EXAMPLE 64

Using a procedure analogous to that described in Example 57, 2-(2'-methoxy-4'-methylsulfonyl-phenyl)-1H-imidazo[4,5-b]pyridine, was prepared from 2-(2'-methoxy-4'-methylmercapto-phenyl)-1H-imidazo[4,5-b]pyridine hydrochloride. Its hydrochloride had a melting point of 240°–242° C.

EXAMPLE 65

Using a procedure analogous to that described in Example 63, 2-(2'-methoxy-4'-ethylsulfinyl-phenyl)-1H-imidazo[4,5-b]pyridine, was prepared from 2-(2'-methoxy-4'-ethylmercapto-phenyl)-1H-imidazo[4,5-b]pyridine. Its hydrochloride had a melting point of 121°–123° C.

EXAMPLE 66

Using a procedure analogous to that described in Example 63, 2-[2'-β-methylsulfinyl-ethoxy)-4'-methylmercapto-phenyl]-1H-imidazo[4,5-b]pyridine, m.p. 191°–192° C (from acetone), was prepared from 2-[2-(2-methylmercapto-ethoxy)-4-methylmercapto-phenyl]-1H-imidazo[4,5-b]pyridine and 1 equivalent of 3-chloro-perbenzoic acid.

EXAMPLE 67

Using a procedure analogous to that described in Example 63, 2-[2'-(β-methylsulfinyl-ethoxy)-4'-methylsulfinyl-phenyl]-1H-imidazo[4,5-b]pyridine, m.p. 190°–191° C, was prepared from 2-[2'-(B-methylsulfinyl-ethoxy)-4'-methylmercapto-phenyl]-1H-imidazo[4,5-b]pyridine and 1 equivalent of 3-chloro-perbenzoic acid.

EXAMPLE 68

Using a procedure analogous to that described in Example 58b, 2-[2'-(β-methylsulfinyl-ethoxy)-4'-methyl-phenyl]-1H-imidazo[4,5-b]pyridine, was prepared from 2-[2'-(β-methylmercapto-ethoxy)-4'-methyl-phenyl]-1H-imidazo[4,5-b]-pyridine hydrochloride. Its hydrochloride had a melting point of 191°–192° C (from acetone/ether).

EXAMPLE 69

Using a procedure analogous to that described in Example 58b, 2-[2'-β-methylsulfinyl-ethoxy)-4'-chlorophenyl]-1H-imidazo[4,5-b]pyridine, was prepared from 2-[2'-(β-methylmercapto-ethoxy)-4'-chloro-phenyl]-1H-imidazo[4,5-b]-pyridine hydrochloride. Its hydrochloride had a melting point of 221°–222° C (from acetone/ether).

EXAMPLE 70

Using a procedure analogous to that described in Example 58, 2-[2'-methoxy-4'-(β-methylsulfinyl-ethoxy)-phenyl]-1H-imidazo[4,5-b]pyridine, was prepared from 2-[2'-methoxy-4'-(β-methylmercapto-ethoxy)-phenyl]-1H-imidazo[4,5-b]pyridine hydrochloride. Its hydrochloride had a melting point of 204°–205° C.

EXAMPLE 71

Using a procedure analogous to that described in Example 58b, 2-[2'-methoxy-4'-(β-ethylsulfinyl-ethoxy)-phenyl]-1H-imidazo[4,5-b]pyridine, was prepared from 2-[2'-methoxy-4'-(β-ethylmercapto-ethoxy)-phenyl]-1H-imidazo[4,5-b]pyridine hydrochloride. Its hydrochloride had a melting point of 217°–219° C.

EXAMPLE 72

Using a procedure analogous to that described in Example 58b, 2-[2'-methoxy-4'-(3''-methylsulfinyl-propoxy)-phenyl]-1H-imidazo[4,5-b]pyridine, was prepared from 2-[2'-methoxy-4'-(3''-methylmercapto-propoxy)-phenyl]-1H-imidazo[4,5-b]pyridine hydrochloride. Its hydrochloride had a melting point of 179°–180° C.

EXAMPLE 73

Using a procedure analogous to that described in Example 58b, 2-[2'-methoxy-4'-(3''-ethylsulfinypropoxy)-phenyl]-1H-imidazo[4,5-b]pyridine, ws prepared from 2-[2'-methoxy-4'-(3''-ethylmercapto-propoxy)-phenyl]-1H-imidazo[4,5-b]pyridine hydrochloride. Its hydrochloride had a melting point of 167°–168° C.

EXAMPLE 74

Using a procedure analogous to that described in Example 63, 2-(2'-methoxy-5'-methylsulfinyl-phenyl)-1H-imidazo[4,5-b]pyridine, was prepared from 2-(2'-methoxy-5'-methylmercapto-phenyl)-1H-imidazo[4,5-b]pyridine hydrochloride. Its hydrochloride had a melting point of 211°–212° C.

EXAMPLE 75

Using a procedure analogous to that described in Example 57, 2-(2'-methoxy-5'-methylsulfonyl-phenyl)-1H-imidazo[4,5-b]pyridine, was prepared from 2-(2'-methoxy-5'-methylmercapto-phenyl)-1H-imidazo[4,5-b]pyridine hydrochloride. Its hydrochloride had a melting point of 240°–241° C.

EXAMPLE 76

2-(2',4'-Dimethoxy-phenyl)-1H-imidazo[4,5-b]pyridine-oxide-(4)

1 gm of 2-(2,4-dimethoxy-phenyl)-1H-imidazo[4,5-b]pyridine and 1.35 gm of 3-chloro-perbenzoic acid were stirred for 15 hours at 60° C in 15 ml of glacial acetic acid. Subsequently, the mixture was recrystallized from 2N acetic acid in the presence of activated charcoal. Further purification was effected by boiling in acetone. The compound had a melting point of 266°–267° C.

EXAMPLE 77

Using a procedure analogous to that described in Example 2, 2-(2'-methoxy-4'-benzyloxy-phenyl)-1H-imidazo[4,5-b]pyridine, was prepared from 2-methoxy-4-benzyloxy-benzoic acid morpholide and 2,3-diamino-pyridine. Its hydrochloride, m.p. 218°–219° C (decomp.), had the formula

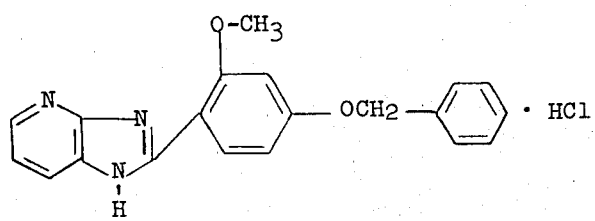

EXAMPLE 78

Using a procedure analogous to that described in Example 2, 2-(2'-methoxy-4'-hydroxy-phenyl)-1H-imidazo[4,5-b]pyridine, was prepared from 2-methoxy-4-hydroxy-benzoic acid morpholide and 2,3-diamino-pyridine. Its hydrochloride had a melting point of 230°–231° C.

EXAMPLE 79

Using a procedure analogous to that described in Example 2, 2-(2'-ethoxy-4'-ethylmercapto-phenyl)-1H-imidazo[4,5-b]pyridine, was prepared from 2-ethoxy-4-ethylmercaptobenzoic acid-morpholide and 2,3-diamino-pyridine. Its hydrochloride had a melting point of 198°–199° C (decomp.)

EXAMPLE 80

Using a procedure analogous to that described in Example 1, 2-(2'-fluoro-4'-methoxy-phenyl)-1H-imidazo[4,5-b]pyridine, was prepared from 2-fluoro-4-methoxy-benzoic acid and 2,3-diamino-pyridine. Its hydrochloride, m.p. 237°–238° C (decomp.), had the formula

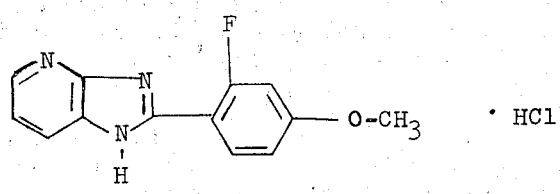

EXAMPLE 81

Using a procedure analogous to that described in Example 1, 2-(4'-fluro-2'-methoxy-phenyl)-1H-imidazo[4,5-b]pyridine, was prepared from 4-fluoro-2-methoxy-benzoic acid and 2,3-diamino-pyridine. Its hydrochloride had a melting point of 235°–236° C (decomp.).

EXAMPLE 82

Using a procedure analogous to that described in Example 1, 2-(2',4'-dimethyl-phenyl)-1H-imidazo[4,5-b]pyridine, was prepared from 2,4-dimethyl-benzoic acid and 2,3-diamino-pyridine. Its hydrochloride had a melting point of 185° C.

EXAMPLE 83

Using a procedure analogous to that described in Example 1, 2-(4'-amino-phenyl)-1H-imidazo[4,5-b]pyridine, was prepared from 4-acetamino-benzoic acid and 2,3-diaminopyridine. Subsequent heating for 15 minutes with 2N hydrochloric acid produced the dihydrochloride, m.p. >300° C.

EXAMPLE 84

2-(2,6-Dimethoxy-phenyl)-1H-imidazo[4,5-b]pyridine and its hydrochloride 9.1 gm of 2,6-dimethoxy-benzoic acid and 5.5 gm of 2,3-diamino-pyridine were refluxed for 3 hours in 100 ml of phosphorus oxychloride. Subsequently, the phosphorus oxychloride was distilled off and the residue was carefully decomposed with ice water. The obtained solution was filtered, neutralized with potassium carbonate and made alkaline with concentrated ammonia. The formed suspension was extracted three times with chloroform, the chloroform layer was dried over magnesium sulfate, and filtered. The solvent was removed and the residue was dissolved in 50 ml of methanolic hydrochloric acid. Subsequently, 100 ml of isopropanol were added, and the product was kept in the deep freezer overnight. The precipitate, the hydrochloride, m.p. 250°–254° C, of the formula

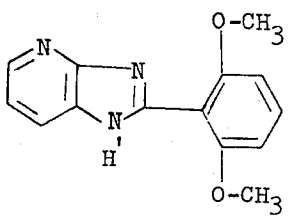

was vacuum filtered and washed with ether.

EXAMPLE 85

Using a procedure analogous to that described in Example 84, 2-(2'-propoxy-4'-methyl-phenyl)-1H-imidazo[4,5-b]pyridine, was prepared from 2-propoxy-4-methyl-benzoic acid morpholide. Its hydrochloride had a melting point of 221°–223° C (decomp.).

EXAMPLE 86

Using a procedure analogous to that described in Example 84, 2-(2'-butoxy-4'-methyl-phenyl)-1H-imidazo[4,5-b]pyridine, was prepared from 2-butoxy-4-methyl-benzoic acid morpholide. Its hydrochloride had a melting point of 211°–213° C (decomp.).

EXAMPLE 87

Using a procedure analogous to that described in Example 84, 2-(4'-methylmercapto-phenyl-1H-imidazo[4,5-b]pyridine, was prepared from 4-methyl-mercapto-benzoic acid. Its hydrochloride had a melting point of 230°–232° C.

EXAMPLE 88

2-[2'-($\beta$-Methylmercapto-ethoxy)-5'-methylmercapto-phenyl]-1H-imidazo[4,5-pyridine and its hydrochloride 50 gm of S-methyl-[2-($\beta$-methylmercapto-ethoxy)-5-methylmercapto]-thiobenzoic acid-morpholide-iodide (obtained by reaction of [2-($\beta$-methylmercapto-ethoxy)-5-methylmercapto]-thiobenzoic acid morpholide with methyl iodide in methanol) and 15 gm of 2,3-diamino-pyridine were heated for 3 hours at 130° C in 150 ml of glycol. After cooling, the mixture was diluted with water and 30 ml of concentrated ammonia were added. Subsequently, the mixture was extracted with chloroform; the organic layer was washed with water, and 2N hydrochloric acid was added. The precipitate, the hydrochloride, m.p. 190°–191° C, was vacuum filtered and recrystallized from methanol.

EXAMPLE 89

Using a procedure analogous to that described in Example 84, 2-(2'-methoxy-4'-propylmercapto-phenyl)-1H-imidazo[4,5-b]pyridine, was prepared from 2-methoxy-4-propylmercapto-benzoic acid-morpholide. Its hydrochloride had a melting point of 203°–204° C (decomp.).

EXAMPLE 90

Using a procedure analogous to that described in Example 84, 2-(2'-ethoxy-4'-propylmercapto-phenyl)-1H-imidazo[4,5-b]pyridine, was prepared from 2-ethoxy-4-propylmercapto-benzoic acid morpholide. Its hydrochloride had a melting point of 182°–183° C.

EXAMPLE 91

Using a procedure analogous to that described in Example 84, 2-(2'-methoxy-4'-butylmercapto-phenyl)-1H-imidazo[4,5-b]pyridine, was prepared from 2-methoxy-4-butylmercapto-benzoic acid morpholide. Its hydrochloride had a melting point of 203°–204° C.

EXAMPLE 92

Using a procedure analogous to that described in Example 84, 2-(2'-ethoxy-4'-butylmercapto-phenyl)-1H-imidazo[4,5-b]pyridine, was prepared from 2-ethoxy-4-butylmercaptobenzoic acid morpholide. Its hydrochloride had a melting point of 207°–208° C.

EXAMPLE 93

2-(4'-Methylsulfinyl-phenyl)-1H-imidazo[4,5-b]pyridine 5.9 gm of 2-(4-methylmercapto-phenyl)-1H-imidazo[4,5-b]pyridine hydrochloride were dissolved in 100 ml of glacial acetic acid and 2.4 gm of 30% hydrogen peroxide were added at 10° C. Subsequently, the mixture was stirred for 3 hours, left standing overnight in the refrigerator and for 10 hours at room temperature. Then the mixture was made alkaline with ammonia and extracted several times with chloroform. The starting material was separated by column chromatography. The residue was suspended in acetone, and the formed crystals were vacuum filtered, yielding 2-(4'-methylsulfinyl-phenyl)-1H-imidazo[4,5-b]pyridine, m.p. 240°–242° C.

EXAMPLE 94

Using a procedure analogous to that described in Example 93, 2-(2'-ethoxy-5'-methylsulfinyl-phenyl)-1H-imidazo[4,5-b]pyridine, m.p. 197°–198° C, was prepared from 2-(2'-ethoxy-5'-methylmercapto-phenyl)-1H-imidazo[4,5-b]pyridine.

EXAMPLE 95

Using a procedure analogous to that described in Example 93, 2-[2'-($\beta$-methylsulfinyl-ethoxy)-5'-methylmercapto-phenyl]-1H-imidazo[4,5-b]pyridine, m.p. 189°–190° C, was prepared from 2-[2'-($\beta$-methylmercapto-ethoxy)-5'-methylmercapto-phenyl]-1H-imidazo[4,5-b]pyridine hydrochloride.

EXAMPLE 96

Using a procedure analogous to that described in Example 93, 2-(2'-ethoxy-4'-ethylsulfinyl-phenyl)-1H-imidazo[4,5-b]pyridine, m.p. 166°–167° C, was prepared from 2-(2'-ethoxy-4'-ethylmercapto-phenyl)-1H-imidazo[4,5-b]pyridine hydrochloride.

EXAMPLE 97

Using a procedure analogous to that described in Example 93, 2-(2'-methoxy-4'-propylsulfinyl-phenyl)-1H-imidazo[4,5-b]pyridine, 182°–183° C, was prepared from 2-(2'-methoxy-4'-propylmercapto-phenyl)-1H-imidazo[4,5-b]pyridine hydrochloride.

EXAMPLE 98

Using a procedure analogous to that described in Example 93, 2-(2'-ethoxy-4'-propylsulfinyl-phenyl)-1H-imidazo[4,5-b]pyridine, m.p. 182°–183° C (decomp.), was prepared from 2-(2'-ethoxy-4'-propylmercapto-phenyl)-1H-imidazo[4,5-b]pyridine hydrochloride.

EXAMPLE 99

Using a procedure analogous to that described in Example 93, 2-(2'-ethoxy-4'-butylsulfinyl-phenyl)-1H-imidazo[4,5-b]pyridine, m.p. 185°–186° C, was prepared from 2-(2'-ethoxy-4'-butylmercapto-phenyl)-1H-imidazo[4,5-b]pyridine hydrochloride.

EXAMPLE 100

2-(4'-Methylsulfonyl-phenyl)-1H-imidazo[4,5-b]pyridine and its hydrochloride 6.95 gm of 2-(4'-methylmercapto-phenyl)-1H-imidazo[4,5-b]pyridine hydrochloride were dissolved in 100 ml of glacial acetic acid. 8.5 gm of 30% hydrogen peroxide were added, and the mixture was left standing for 4 days at room temperature. After purification on a silicagel column, the residue was dissolved in acetone. The hydrochloride, m.p. 286° C, was precipitated by addition of methanolic hydrochloric acid.

EXAMPLE 101

2-(2'-Ethoxy-4'-ethylsulfonyl-phenyl)-1H-imidazo[4,5-b]pyridine 400 mgm of 2-(2'-ethoxy-4'-ethylmercapto-phenyl)-1H-imidazo[4,5-b]pyridine hydrochloride together with 0.5 ml of 30% hydrogen peroxide were dissolved in 30 ml of glacial acetic acid. The mixture was allowed to stand overnight and was then heated for 1 hour at 90° C. After cooling, the mixture was diluted with water, neutralized with sodium bicarbonate, extracted with chloroform and the organic layer was evaporated after drying. The residue was purified by column chromatography, yielding the free base named in the heading, m.p. 207°–208° (from acetone).

EXAMPLE 102

Using a procedure analogous to that described in Example 101, 2-(2'-methoxy-4'-propylsulfonyl-phenyl)-1H-imidazo[4,5-b]pyridine, m.p. 219°–220° C, was prepared from 2-(2'-methoxy-4'-propylmercapto-phenyl)-1H-imidazo[4,5-b]pyridine.

EXAMPLE 103

Using a procedure analogous to that described in Example 101, 2-(2'-ethoxy-4'-butylsulfonyl-phenyl)-1H-imidazo[4,5-b]pyridine, m.p. 156°–157° C, was prepared from 2-(2'-ethoxy-4'-butylmercapto-phenyl)-1H-imidazo[4,5-b]pyridine.

EXAMPLE 104

2-[2'-Methoxy-4'-(β-dimethylamino-ethoxy)-phenyl]-1H-imidazo[4,5pyridine and its dihydrochloride a. 2-[2'-Methoxy-4'-(β-chloroethoxy)-phenyl]-1H-imidazo[4,5-b]pyridine and its hydrochloride 14 gm of 2-methoxy-4-(β-hydroxy-ethoxy)-benzoic acid morpholide were refluxed for 1.5 hours with 7.1 gm of 2,3-diamino-pyridine in 100 ml of phosphorus oxychloride. Subsequently, the mixture was decomposed with ice water, and the gradually crystallizing precipitate, m.p. 266°–268° C (decomp.), was vacuum filtered and washed with acetone.

b. 2 gm of 2-[2'-methoxy-4'-(β-chloroethoxy)-phenyl]-1H-imidazo[4,5-b]pyridine hydrochloride were heated in a closed reaction vessel for 12 hours at 120° C with 5 gm of dimethylamine in 100 ml of ethanol. After evaporation, the residue was purified by column chromatography. The dihydrochloride, m.p. >250° C, was precipitated from acetone by addition of methanolic hydrochloric acid, subsequently recrystallized from methanol, and had the formula

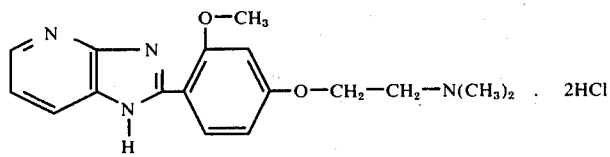

EXAMPLE 105

Using a procedure analogous to that described in Example 104, 2-[2'-methoxy-4'-(3''-dimethylamino-propoxy)-phenyl]-1H-imidazo[4,5-b]pyridine, was prepared from 2-[2'-methoxy-4'-(3''-chloro-propoxy)-phenyl]-1H-imidazo[4,5-b]pyridine hydrochloride. Its dihydrochloride had a melting point of 238°–242° C.

EXAMPLE 106

Using a procedure analogous to that described in Example 104, 2-[2'-methoxy-4'-(3''-diethylamino-propoxy)-phenyl]-1H-imidazo[4,5-b]pyridine, was prepared from 2-[2'-methoxy-4'-(3''-chloropropoxy)-phenyl]-1H-imidazo[4,5-b]pyridine hydrochloride. Its dihydrochloride had a melting point of 222°–224° C.

EXAMPLE 107

Using a procedure analogous to that described in Example 84, 2-(2',6'-dichlorophenyl)-1H-imidazo[4,5-b]pyridine, was prepared from 2,6-dichlorobenzoic acid with purification by column chromatography. Its hydrochloride had a melting point of 262°–264° C (decomp.)

EXAMPLE 108

2-[p-Methoxy-o-(3'-[β-phenethylamino]-propoxy)-phenyl]-1H-imidazo[4,5-b]pyridine and its dihydrochloride 1.77 gm of 2-[p-methoxy-o-(3'-chloropropoxy)-phenyl]-1H-imidazo[4,5-b]pyridine were heated for 1.5 hours in 10 ml of β-phenethylamine at 180° C. The free base, 2-[p-methoxy-o-(3'-[β-phenethylamino]-propoxy)-phenyl]-1H-imidazo[4,5-b]pyridine, was converted into its dihydrochloride with methanolic hydrochloric acid, and was then recrystallized from isopropanol, whereupon it had a melting point of 238° C.

EXAMPLE 109

2-[p-Methoxy-o-(3'-[N-methyl-N-β-phenethyl-amino]-propoxy)-phenyl]-1H-imidazo[4,5-b]pyridine and its dihydrochloride 3.2 gm of 2-[p-methoxy-o-(3'-chloropropoxy)-phenyl]-1H-imidazo[4,5-b]pyridine and 2.7 gm of N- methyl-β-phenethyl-amine were heated for 6 hours in ethanol at 120° C in a closed vessel. The free base, 2-[p-methoxy-o-(3'-[N-methyl-N-2''-phenethylamino]-propoxy)-phenyl]-1H-imidazo[4,5-b]pyridine, was purified by column chromatography. The dihydrochloride was precipitated from ethyl acetate solution of the free base by addition of ethereal hydrochloric acid, and recrystallized from isopropanol, whereupon it had a melting point of 212°–215° C.

EXAMPLE 110

2-[p-Methoxy-o-(3'-[N-methyl-N-(β-3'',4''-dimethoxy-phenethyl)-amino]-propoxy)-phenyl]-1H-imidazo[4,5-b]pyridine and its dihydrochloride 5.0 gm of 2-[p-methoxy-o-(3'-chloropropoxy)-phenyl]-1H-imidazo[4,5-b]pyridine and 8.5 gm of N-[β-(3,4-dimethoxyphenyl)-ethyl]-methylamine were refluxed for 12 hours in ethylene glycol monomethyl ether. The dihydrochloride was precipitated from an ethyl acetate solution of the free base, 2-[p-methoxy-o-(3'-[N-methyl-N-(β-3'',4''-dimethoxy-phenethyl)-amino]-propoxy)-phenyl]-1H-imidazo[4,5-b]pyridine, by addition of ethereal hydrochloric acid. The salt had the formula

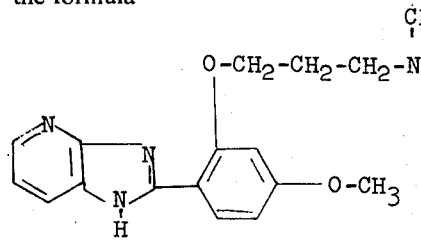

and a melting point of 169° C.

EXAMPLE 111

Using a procedure analogous to that described in Example 109, 2-[p-methoxy-o-(3'-methylamino-propoxy)-phenyl]-1H-imidazo[4,5-b]pyridine, was prepared from 2-[p-methoxy-o-(3'-chloro-propoxy)-phenyl]-1H-imidazo[4,5-b]pyridine and methylamine. Its hydrochloride had a melting point of 215° C.

EXAMPLE 112

Using a procedure analogous to that described in Example 109, 2-[p-methoxy-o-(β-dimethylamino-ethoxy)-phenyl]-1H-imidazo[4,5-b]pyridine, was prepared from 2-[p-methoxy-o-(β-chloroethoxy)-phenyl]-1H-imidazo[4,5-b]pyridine and dimethylamine. Its dihydrochloride had a melting point of 240°–242° C.

EXAMPLE 113

2-(2'-Methylamino-phenyl)-1H-imidazo[4,5-b]pyridine 1.77 gm of N-methyl-isatoic acid anhydride and 1.09 gm of 2,3-diaminopyridine were melted together and heated for 10 minutes at 180° C. The reaction product was recrystallized from ethyl acetate, yielding 2-(2'-methylamino-phenyl)-1H-imidazo[4,5-b]pyridine, m.p. 262°–263° C.

EXAMPLE 114

Using a procedure analogous to that described in Example 84, 2-(2'-fluoro-5'-methylmercapto-phenyl)-1H-imidazo[4,5-b]pyridine, m.p. 195° C, was prepared from 2,3-diaminopyridine and 2-fluoro-5-methylmercapto-benzoic acid.

EXAMPLE 115

2-(2'-Fluoro-5'-methylsulfinyl-phenyl)-1H-imidazo[4,5-b]pyridine 2-(2'-fluoro-5'-methylmercapto-phenyl)-1H-imidazo[4,5-b]pyridine was oxidized with hydrogen peroxide in glacial acetic acid at room temperature. The purification was effected by column chromatography on silicagel with chloroform/methanol (19:1) as the eluant. The free base, 2-(2'-fluoro-5-methylsulfinyl-phenyl)-1H-imidazo[4,5-b]pyridine, had a melting point of 190°–192° C.

EXAMPLE 116

Using a procedure analogous to that described in Example 115, 2-(2'-fluoro-5'-methylsulfonyl-phenyl)-1H-imidazo[4,5-b]pyridine, m.p. 242° C, was prepared from 2-(2'-fluoro-5'-methylmercapto-phenyl)-1H-imidazo[4,5-b]pyridine at 40° C.

EXAMPLE 117

Using a procedure analogous to that described in Example 84, 2-(2'-fluoro-4'-methylmercapto-phenyl-1H-imidazo[4,5-b]pyridine, was prepared from 2-fluro-4-methyl-mercaptobenzoic acid and 2,3-diaminopyridine. Its hydrochloride had a melting point of 257° C.

EXAMPLE 118

Using a procedure analogous to that described in Example 84, 2-(2'-fluorophenyl)-1H-imidazo[4,5-b]pyridine, m.p. 201° C, was prepared from 2-fluorobenzoic acid and 2,3-diaminopyridine.

EXAMPLE 119

Using a procedure analogous to that described in Example 84, 2-(2'-chlorophenyl)-1H-imidazo[4,5-b]pyridine, was prepared from 2-chlorobenzoic acid and 2,3-diaminopyridine. Its hydrochloride had a melting point of 233° C.

EXAMPLE 120

Using a procedure analogous to that described in Example 115, 2-(2'-fluoro-4'-methylsulfinyl-phenyl)-1H-imidazo[4,5-b]pyridine, m.p. 219° C, was prepared from 2-(2'-fluoro-4'-methyl-mercapto-phenyl-1H-imidazo[4,5-b]pyridine. The free base was crystallized by trituration in petroleum ether.

The compounds of the present invention, that is, those embraced by formulas I and Ia above and their non-toxic, pharmacologically acceptable acid addition salts, have useful pharmacodynamic properties. More particularly, they exhibit an altering effect on the blood-pressure, positive inotropic activity, anti-ulcerogenic activity, an inhibiting effect on the platelet aggregation, and a prolonging effect on the bleeding time in warm-blooded animals, such as cats.

The pharmacodynamic activities of the compounds of the present invention (A–J) and those of certain closely related prior art compounds (K–M) were ascertained in the manner described below, and some illustrative test results are shown in the tables, where A = 2-(2',4'-dimethoxy-phenyl)-1H-imidazo[4,5-b]pyridine hydrochloride,
B = 2-[2'-β-methylsulfinyl-ethoxy)-4'-methoxy-phenyl]-1H-imidazo[4,5-b]pyridine hydrochloride,
C = 2-(2'-methoxy-4'-methylmercapto-phenyl)-1H-imidazo[4,5-b]pyridine hydrochloride.
D = 2-(2'-methoxy-4'-methylsulfinyl-phenyl)-1H-imidazo[4,5-b]pyridine hydrochloride,
E = 2-(2'-methoxy-5'-methylmercapto-phenyl)-1H-imidazo[4,5-b]pyridine hydrochloride,
F = 2-(2'-methoxy-4'-methyl-phenyl)-1H-imidazo[4,5-b]pyridine hydrochloride,
G = 2-(2'-ethoxy-4'-methoxy-phenyl)-1H-imidazo[4,5-b]pyridine hydrochloride,
H = 2-(2'-ethoxy-4'-methyl-phenyl)-1H-imidazo[4,5-b]pyridine hydrochloride,
I = 2-(2'-methoxy-4'-chloro-phenyl)-1H-imidazo[4,5-b]pyridine hydrochloride
J = 2-[2'(β-methylsulfinyl-ethoxy)-4'-methylmercapto-phenyl]-1H-imidazo[4,5-b]pyridine hydrochloride,
K = 2-phenyl-1H-imidazo[4,5-b]pyridine hydrochloride,
L = 2-(4'-methyl-phenyl)-1H-imidazo[4,5-b]pyridine, and
M = 2-(4'-chloro-phenyl)-1H-imidazo[4,5-b]pyridine hydrochloride.

Positive inotropic activity in the isolated auricle of the guinea pig:

Isolated auricles of guinea pigs were put into an organ bath of 100 ml. The bath had been filled with a tyrode solution having a temperature of 30° C, carbogen (95% of $O_2$ and 5% of $CO_2$) was bubbled through the tyrode solution. The spontaneous contractions of the auricles were registered isometrically with a Statham-Force-transducer on a Grass-polygraph. The auricles were charged with 1 gm. After sufficient equilibrating time, the compounds to be tested were added to the organ bath. The concentration of each compound in the bath was $1 \times 10^{-5}$ gm/ml each time. For every compound tested 5 auricles were used. The results are shown in the following table:

TABLE I

| Compound | Increase of the contraction amplitude in % |
| --- | --- |
| A | 57.0 |
| B | 17.5 |
| C | 10.3 |
| E | 40.9 |
| F | 50.2 |
| G | 33.9 |
| H | 42.9 |
| I | 21.4 |
| J | 11.4 |

Circulation tests in the anesthetized cat:

Cats were anesthetized with 30 mgm/kg of sodium pentobarbital, i.v. A plastic catheter was introduced into the arteria femoralis, and into the left ventricle of the heart a steel catheter was introduced from the arteria carotis. With Statham-pressure-transducers of the type P23 AA and P23 Dc, the arterial blood-pressure and the pressure in the left ventricle was registered continuously. From the ventricle-pressure curve, the contractility parameters $dp/dt_{max}$ and $V_{CE}$ were continuously determined by means of an analog computer. The heart frequency was ascertained from the ventricle-pressure-curve, using a tachograph. In addition, the EKG was recorded in the II derivation.

All recordings were effected on a Brush-direct-writer. The test substances were injected through a *vena cannula* into the *vena femoralis*. Each compound was tested on at least three cats. The results are shown in the following table:

TABLE II

| Compound | Dose mgm/kg i.v. | Blood-pressure alteration in mm Hg | Heart activity Alteration of the contraction force in % | Alteration of the heart frequency in % |
| --- | --- | --- | --- | --- |
| A | 0.5 | − 5 | + 20 | + 4 |
|   | 1.0 | − 5 | + 41 | + 5 |
| B | 0.5 | + 10 | + 16 | − 2 |
|   | 1.0 | + 20 | + 29 | − 9 |
| C | 0.5 | + 5 | + 22 | + 1 |
|   | 1.0 | + 10 | + 36 | + 5 |
| D | 0.5 | 0 | + 34 | + 5 |
|   | 1.0 | − 5 | + 39 | + 5 |
| E | 0.5 | + 10 | + 14 | 0 |
|   | 1.0 | + 15 | + 25 | 0 |
| F | 0.5 | + 10 | + 44 | − 3 |
|   | 1.0 | + 15 | + 53 | 0 |
| G | 0.5 | 0 | + 7 | 0 |
|   | 1.0 | + 5 | + 29 | − 5 |
| H | 0.5 | + 10 | + 15 | 0 |
|   | 1.0 | + 15 | + 25 | 0 |
| I | 0.5 | − 5 | + 17 | + 2 |
|   | 1.0 | − 5 | + 19 | + 2 |
| J | 0.5 | + 10 | + 14 | 0 |
|   | 1.0 | + 15 | + 22 | − 15 |
| K | 0.5 | 0 | 0 | n.t. |
|   | 2.0 | 0 | 0 | n.t. |
| L | 0.5 | 0 | − 4 | n.t. |
|   | 2.0 | 0 | − 20 | n.t. |
| M | 0.5 | 0 | 0 | n.t. |

TABLE II-continued

| Compound | Dose mgm/kg i.v. | Blood-pressure alteration in mm Hg | Heart activity | |
|---|---|---|---|---|
| | | | Alteration of the contraction force in % | Alteration of the heart frequency in % |
| | 2.0 | 0 | −10 | n.t. | n.t. = not tested

None of the compounds embraced by formulas I and Ia showed any toxic side effects at the applied dosage levels.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.584 to 3.33 mgm/kg body weight, preferably 0.833 to 1.67 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 121

Tablets

The tablet composition was compounded from the following ingredients:

| | | |
|---|---|---|
| 2-(2',4',-Dimethoxy-phenyl)-1H-imidazo [4,5-b]pyridine hydrochloride | | 100.0 parts |
| Lactose | | 50.0 parts |
| Polyvinyl pyrrolidone | | 5.0 parts |
| Carboxymethylcellulose | | 19.0 parts |
| Magnesium stearate | | 1.0 parts |
| | Total | 175.0 parts |

Preparation:

The imidazopyridine compound, the lactose and the carboxymethyl cellulose were admixed, the mixture was moistened with an aqueous solution of the polyvinylpyrrolidone, the moist mass was granulated through a 1.5 mm-mesh screen, the granulate was dried at 50° C and again passed through a 1 mm-mesh screen, the dry granulate was admixed with the magnesium stearate, and the composition was compressed into 175 mgm-tablets. Each tablet contained 100 mgm of the imidazopyridine compound and was an oral dosage unit composition with effective cardiotonic and anticoagulant action.

EXAMPLE 122

Coated pills

The pill core composition was compounded from the following ingredients:

| | |
|---|---|
| 2-[2'-Methylsulfinyl-ethoxy-4'-methoxy-phenyl]-1H-imidazo[4,5-b]pyridine hydrochloride | 50.0 parts |
| Corn starch, dry | 20.0 parts |

-continued

| | | |
|---|---|---|
| Soluble starch | | 2.0 parts |
| Carboxymethylcellulose | | 7.0 parts |
| Magnesium stearate | | 1.0 parts |
| | Total | 80.0 parts |

Preparation:

The imidazopyridine compound was admixed with the corn starch, the mixture ws kneaded intensely with an aqueous solution of the soluble starch and then granulated and dried at 50° C in a circulating drier in a conventional manner. The granulate was admixed with the remaining excipients and compressed into 80 mgm-pill cores. The cores were coated with a thin shell consisting of talcum, sugar and polished with beeswax in known manner. Each coated pill contained 50 mgm of the imidazopyridine compound and was an oral dosage unit composition with effective cardiotonic and anticoagulant action.

EXAMPLE 123

Suppositories

The suppository composition was compounded from the following ingredients:

| | | |
|---|---|---|
| 2-(2'-Methoxy-4'-methylmercapto-phenyl)-1H-imidazo[4,5-b]pyridine hydrochloride | | 75.0 parts |
| Suppository base (e.g. cocoa butter) | | 1625.0 parts |
| | Total | 1700.0 parts |

Preparation:

The imidazopyridine compound was dispersed homgeneously in the molten suppository base at 38° C and cooled to 35° C. 1700 mgm portions of the mixture were poured into cooled suppository molds, and allowed to solidify. Each suppository contained 75 mgm of the imidazopyridine compound and was a rectal dosage unit composition with effective cardiotonic and anticoagulant action.

EXAMPLE 124

Hypodermic solution

The hypodermic solution was compounded from the following ingredients:

| | |
|---|---|
| 2-(2'-Methoxy-4'-methylsulfinyl-phenyl)-1H imidazo[4,5-b]pyridine hydrochloride | 50.0 parts |
| Sorbitol | 250.0 parts |
| Distilled water q.s.ad | 5000.0 parts by vol. |

Preparation:

The active ingredient and the sorbitol were dissolved in distilled water. The solution was diluted with distilled water to the indicated volume and filtered until free of fibers. The solution was filled into white 5 ml-ampules and sterilized for 20 minutes at 120° C. Each ampule contained 50.0 mgm of the imidazopyridine compound and its contents were an injectable dosage unit composition with effective cardiotonic and anticoagulant action.

EXAMPLE 125

Drop Solution

The drop solution was compounded from the following ingredients:

| | | |
|---|---|---|
| 2-(2'-Methoxy-5'-methylmercapto-phenyl)-1H-imidazo[4,5-b]pyridine hydrochloride | 0.5 | parts |
| Methyl-p-hydroxybenzoate | 0.035 | parts |
| Propyl-p-hydroxybenzoate | 0.015 | parts |
| Anise oil | 0.05 | parts |
| Menthol | 0.06 | parts |
| Sodium saccharin | 1.0 | parts |
| Glycerin | 10.0 | parts |
| Ethanol | 40.0 | parts |
| Distilled water q.s.ad | 100.0 | parts by vol. |

Preparation:

The benzoic acid esters were dissolved in ethanol and subsequently the anise oil and the menthol were added. The active ingredient, glycerin and sodium saccharin were dissolved in water and added. The solution was filtered until free of fibers. 5 ml of the drop solution (about 100 drops) contained 25 mgm of the imidazopyridine compound and was an oral dosage unit composition with effective cardiotonic and anticoagulant action.

Analogous results are obtained when any one of the other imidazopyridine compounds embraced by formulas I and Ia, or a non-toxic, pharmacologically acceptable acid addition salt thereof, is substituted for the particular imidazopyridine compound in Examples 121–125. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention of the scope of the appended claims.

We claim:

1. A compound of the formula

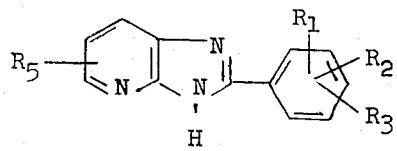

or

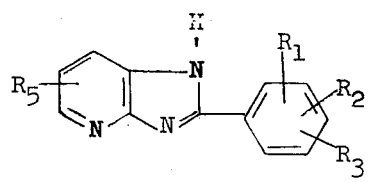

wherein $R_1$ is alkoxy of 1 to 4 carbon atoms, allyloxy, benzyloxy, methoxy-ethoxy, methylthio, methylsulfinyl, methylsulfonyl or methylsulfinyl-ethoxy, $R_2$ is hydrogen, hydroxyl, methyl, methoxy, ethoxy, fluorine, chlorine, (alkyl of 1 to 4 carbon atoms)-thio, (alkyl of 1 to 4 carbon atoms)-sulfinyl, (alkyl of 1 to 4 carbon atoms)-sulfinyl, (alkyl of 1 to 4 carbon atoms)-sulfonyl of Z—A—O where A is alkylene of 2 to 3 carbon atoms, and Z is chlorine, hydroxyl, methylthio, ethylthio, methylsulfinyl, ethylsulfinyl, methylsulfonyl or ethylsulfonyl, $R_3$ is hydrogen or methoxy, or any two of $R_1$, $R_2$ and $R_3$ together are methylenedioxy, and $R_5$ is hydrogen, chlorine or methyl, or a non-toxic, pharmacologically acceptable acid addition salt thereof.

2. A compound of claim 1, wherein $R_1$ is methoxy, ethoxy, methylthio or methoxy-ethoxy, $R_2$ is methyl, methoxy, ethoxy, fluorine, methylthio, ethylthio, methylsulfinyl, ethylsulfinyl, methylsulfonyl, ethylsulfonyl or (alkyl of 1 to 2 carbon atoms)-sulfinyl-(alkoxy of 2 to 3 carbon atoms), and $R_3$ and $R_5$ are hydrogen, or a non-toxic, pharmacologically acceptable acid addition salt thereof.

3. A compound of claim 1, which is 2-(2',4'-dimethoxy-phenyl)-1H-imidazo[4,5-b]pyridine, or a non-toxic, pharmacolgocally acceptable acid addition salt thereof.

4. A compound of claim 1, which is 2-[2'-β-methylsulfinyl-ethoxy)-4'-methoxy-phenyl]-1H-imidazo[4,5-b]pyridine, or a non-toxic, pharmacologically acceptable acid addition salt thereof.

5. A compound of claim 1, which is 2-(2'-methoxy-4'-methylmercapto-phenyl)-1H-imidazo[4,5-b]pyridine, or a non-toxic, pharmacologically acceptable acid addition salt thereof.

6. A compound of claim 1, which is 2-(2'-methoxy-4'-methylsulfinyl-phenyl)-1H-imidazo[4,5-b]pyridine, or a non-toxic, pharmacologically acceptable acid addition salt thereof.

7. A compound of claim 1, which is 2-(2'-methoxy-5'-methylmercapto-phenyl)-1H-imidzo[4,5-b]pyridine, or a non-toxic, pharmacologically acceptable acid addition salt thereof.

8. A compound of claim 1, which is 2-(2'-methoxy-4'-methyl-phenyl)-1H-imidazo[4,5-b]pyridine, or a non-toxic, pharmacologically acceptable acid addition salt thereof.

9. A compound of claim 1, which is 2-(2'-ethoxy-4'-methoxy-phenyl)-1H-imidazo[4,5-b]pyridine, or a non-toxic, pharmacologically acceptable acid addition salt thereof.

10. A compound of claim 1, which is 2-(2'-ethoxy-4'-methyl-phenyl)-1H-imidazo[4,5-b]pyridine, or a non-toxic, pharmacologically acceptable acid addition salt thereof.

11. A compound of claim 1, which is 2-(2'-methoxy-4'-chloro-phenyl)-1H-imidazo[4,5-b]pyridine, or a non-toxic, pharmacologically acceptable acid addition salt thereof.

12. A pharmaceutical dosage unit composition consisting essentially of an inert pharmaceutical carrier and an effective cardiotonic or anticoagulant amount of a compound of claim 1.

13. The method of producing a tonic effect on the heart and delaying coagulation of the blood in a warm-blooded animal in need of such treatment, which comprises perorally or parenterally administering to said animal an effective cardiotonic and anticoagulant of a compound of claim 1.

* * * * *